(12) United States Patent
Cheng et al.

(10) Patent No.: US 10,196,665 B2
(45) Date of Patent: Feb. 5, 2019

(54) CELL CULTURE MEDIUM AND METHODS FOR ENHANCING RECOMBINANT ANTIBODY PURITY

(71) Applicant: Sunshine Lake Pharma Co., Ltd., Dongguan, Guangdong (CN)

(72) Inventors: Xiwen Cheng, Dongguan (CN); Chengwei Yan, Dongguan (CN); Bin Yang, Dongguan (CN); Wen-Chen Suen, Irvine, CA (US); Yuancan Weng, Dongguan (CN); Chongfei Deng, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 136 days.

(21) Appl. No.: 15/405,327

(22) Filed: Jan. 13, 2017

(65) Prior Publication Data
US 2018/0030495 A1  Feb. 1, 2018

(51) Int. Cl.
*C12N 5/00* (2006.01)
*C12P 21/00* (2006.01)

(52) U.S. Cl.
CPC .......... *C12P 21/005* (2013.01); *C12N 5/0018* (2013.01); *C12N 5/0037* (2013.01); *C12N 5/0043* (2013.01); *C12P 21/00* (2013.01); *C12N 2500/32* (2013.01)

(58) Field of Classification Search
None
See application file for complete search history.

(56) References Cited

U.S. PATENT DOCUMENTS

| 5,118,618 | A | * | 6/1992 | Kendall | ............. | C07K 16/1228 |
|---|---|---|---|---|---|---|
| | | | | | | 435/326 |
| 5,593,822 | A | * | 1/1997 | Zeng | ................... | C12N 5/0018 |
| | | | | | | 435/2 |
| 5,672,502 | A | | 9/1997 | Birch et al. | | |
| 5,986,048 | A | | 11/1999 | Rubroder et al. | | |
| 6,380,355 | B1 | | 4/2002 | Rubroder et al. | | |
| 6,727,346 | B2 | | 4/2004 | Rubroder et al. | | |
| 7,928,205 | B2 | | 4/2011 | Dillon et al. | | |
| 8,053,236 | B2 | | 11/2011 | Morris et al. | | |
| 8,093,045 | B2 | | 1/2012 | Pla | | |
| 8,252,557 | B2 | | 8/2012 | Katayama et al. | | |
| 8,663,945 | B2 | | 3/2014 | Pla | | |
| 8,765,413 | B2 | | 7/2014 | Joosten et al. | | |
| 8,906,646 | B2 | | 12/2014 | Pla et al. | | |
| 8,911,964 | B2 | | 12/2014 | Pla et al. | | |
| 9,073,988 | B2 | | 7/2015 | Pla et al. | | |
| 9,090,867 | B2 | | 7/2015 | Pla et al. | | |
| 9,133,493 | B2 | | 9/2015 | Jerums et al. | | |
| 9,228,168 | B2 | | 1/2016 | Morris et al. | | |
| 9,234,032 | B2 | | 1/2016 | Pla | | |
| 9,284,371 | B2 | | 3/2016 | Pla et al. | | |
| 9,388,447 | B2 | | 7/2016 | Jerums et al. | | |
| 2002/0012991 | A1 | * | 1/2002 | Fong | ...................... | C07K 16/00 |
| | | | | | | 435/325 |
| 2011/0137012 | A1 | | 6/2011 | Katayama et al. | | |
| 2011/0229933 | A1 | | 9/2011 | Krishnan et al. | | |
| 2014/0134674 | A1 | | 5/2014 | Matuck | | |
| 2015/0125905 | A1 | | 5/2015 | Pla et al. | | |
| 2015/0337258 | A1 | | 11/2015 | Von Hagen et al. | | |
| 2016/0060591 | A1 | | 3/2016 | Morris et al. | | |
| 2016/0186130 | A1 | | 6/2016 | Pla et al. | | |

FOREIGN PATENT DOCUMENTS

| CN | 1557948 | A | 12/2004 |
|---|---|---|---|
| CN | 1238498 | C | 1/2006 |
| CN | 102911958 | A | 2/2013 |
| CN | 103361355 | A | 10/2013 |
| CN | 104560882 | A | 4/2015 |

OTHER PUBLICATIONS

G.W.Hiller et al.,Transient responses of hybridoma cells in continuous culture to step changes in amino acid and vitamin concentrations,Biotechnology and Bioengineering,vol. 44,No. 3,Jul. 1, 1994,303-321.
Zhu D et al.,Optimization of the culture medium composition for the antibody response of mouse spleen cells,In Vitro Aug. 1984,vol. 20,No. 8,Aug. 1984,615-622.
Stephen F Gorfien et al.,Optimized Nutrient Additives for Fed-batch Cultures,Biopharm International,Advanstar Communictions,Duluth,MN,US,Apr. 1, 2003,pp. 34-40.
Anonymous,CHO Medium Component Optimization Kit 2,pp. 1-10.
European Search Report of EP17151743.

* cited by examiner

*Primary Examiner* — Blaine Lankford
(74) *Attorney, Agent, or Firm* — Kam Wah Law (57) ABSTRACT

This invention relates to a novel cell culture medium and methods to enhance recombinant antibody purity using the cell culture medium disclosed herein. The novel cell culture medium is a self-made feeding medium, which comprises from about 90 nM to about 500 mM cysteine, from about 50 mM to about 500 mM tyrosine, and from about 50 mM to about 300 tryptophan. This invention also relates to a method of growing cell culture using the cell culture medium disclosed herein By controlling the concentration of cysteine in the self-made feed medium as well as the amount and time of adding this feed medium into the cell culture, the purity of antibodies is significantly improved while glycosylation profile and antibody expression level are consistently maintained to guarantee the efficacy of antibodies.

13 Claims, 4 Drawing Sheets

CELL CULTURE MEDIUM AND METHODS FOR ENHANCING RECOMBINANT ANTIBODY PURITY

CROSS-REFERENCE TO RELATED APPLICATION

This application claims priority to PCT Application No. PCT/CN2016/092322, filed on Jul. 29, 2016, which is hereby incorporated by reference in its entirety.

FIELD OF TECHNOLOGY

The invention relates to the biotechnology field, and specifically involves a novel cell culture medium and methods for enhancing recombinant antibody purity using the cell culture medium disclosed herein.

BACKGROUND OF THE INVENTION

In the biopharmaceutical industry, the expression of complex recombinant protein drugs in mammalian cells (MC) has obvious advantages. MC can complete suitable post translation modification to ensure that the expressed recombinant proteins have formed proper disulfide bonds, glycosylation pattern and other complex protein structure to guarantee the safety and efficacy of these protein drugs. MC therefore is an important kind of expression system.

In recent years, animal cell culture technology for producing monoclonal antibodies in large-scale has been advanced rapidly. Technical progress in the field is mainly concentrated in the personalized media development and the process condition optimization, etc. Recombinant antibodies as one kind of biological macromolecules may have various forms due to aggregation, degradation, glycosylation modification, oxidation, acetoxylation, isomerization, and mismatched disulfide bonds. Purity of antibody is a decisive factor on the safety and efficacy of antibody molecules. Existing methods for improving antibody purity are mainly focusing on shortening the growth duration time of cell culture or modifying downstream purification methodology to increase purity but sacrifice yield. Decreasing cell culture duration time will reduce the final harvested antibody amount, and may also affect glycosylation pattern. Modifying downstream purification methodology may increase purity but sacrifice yield. As a result, novel cell culture approaches to significantly improve the antibody purity without reducing the final antibody product yield are needed.

SUMMARY OF THE INVENTION

The purpose of the present invention is to provide a kind of self-made feed medium and culture methods to achieve high purity antibody expression in cell culture, especially in mammalian cell culture.

In one aspect, provided herein is a self-made feed medium used in mammalian cell culture, the self-made feed medium comprises from about 90 mM to about 500 mM of cysteine, and about 50 mM to about 500 mM of tyrosine, and about 50 mM to about 300 mM of tryptophan.

In some embodiments, the concentration of cysteine is from about 100 mM to about 400 mM, or from 120 mM to about 300 mM.

In some embodiments, the concentration of tyrosine is from about 100 mM to about 500 mM, or from about 200 mM to about 400 mM, or from about 250 mM to about 350 mM, and the concentration of the tryptophan is from about 50 mM to about 200 mM, or from about 50 mM to about 150 mM.

In certain embodiments, the self-made feed medium is a liquid medium having a pH equal or greater than about 10, or ranging from about 10 to about 12.

In some embodiments, the preparation method of the self-made feed medium includes the following steps: dissolving predetermined amount of cysteine, tyrosine and tryptophan in water, adjusting the pH to from about 10 to about 12, and diluting with water to 1 L. The whole preparation process is conducted under constant stirring and away from light condition or without light. In certain embodiments, the pH is adjusted with NaOH. The concentration of cysteine is from about 90 mM to about 500 mM, or from about 100 mM to about 400 mM, or from about 120 mM to about 300 mM, and the concentration of tyrosine is from about 50 mM to about 500 mM, or from about 100 mM to about 500 mM, or from about 200 mM to about 400 mM, or from about 250 mM to about 350 mM, and the concentration of the tryptophan is from about 50 mM to about 300 mM, or from about 50 mM to about 200 mM, or from about 50 mM to about 150 mM. In another aspect, provided herein is a cell culture method for high purity antibody expression in cell cultures, especially in mammalian cell cultures. The cell culture method involves the addition of the self-made feed medium into cell culture at the exponential growth phase.

In some embodiments, the cell culture method comprises the following steps:

(1) seeding mammalian cells comprising a nucleic acid encoding the antibody of interest in a basal cell culture medium disclosed herein to form a cell culture.

(2) adding the self-made feed medium after the cell culture entering the exponential phase; and (3) monitoring cell viability and adjusting the culture duration time.

In certain embodiments, the basal cell culture medium used in step (1) has the following characteristics: 1) it has no serum and protein components; and 2) it is used in mammalian cell culture.

In some embodiments, the basal cell culture medium used in step (1) is selected from one or more of the following commercial medium: Hycell CHO Medium, CD FortiCHO™ AGT™ Medium, Dynamic™ AGT™ Medium, CDM4 PERMAb, TFS-RDMP-1, and TFS-RDMP-9. In certain embodiments, the basal cell culture medium is CD FortiCHO™ AGT™ Medium, Hycell CHO Medium or a combination thereof.

In some embodiments, the mammalian cells used in step (1) are Chinese Hamster Ovary (CHO) cells.

In certain embodiments, the self-made feed medium comprises from about 90 mM to about 500 mM of cysteine, from about 50 mM to about 500 mM of tyrosine, and from about 50 mM to about 300 of tryptophan. In further embodiments, the concentration of cysteine is from about 100 mM to about 400 mM, or from about 120 mM to about 300 mM, and the concentration of tyrosine is from about 50 mM to about 500 mM, or from about 100 mM to about 500 mM, or from about 200 mM to about 400 mM, or from about 250 mM to about 350 mM, and the concentration of the tryptophan is from about 50 mM to about 300 mM, or from about 50 mM to about 200 mM, or from about 50 mM to about 150 mM.

In some embodiments, the preparation method of the self-made feed medium includes the following steps: dissolving cysteine, tyrosine and tryptophan in water, adjusting the pH to about 10 to 12, and diluting with water to 1 L. The whole preparation process is conducted under constant stirring and away from light condition. In certain embodiments, the pH is adjusted with NaOH. In further embodiments, the concentration of the cysteine is from about 90 mM to about 500 Mm, from about 100 mM to about 400 mM, or from about 120 mM to about 300 mM. In still further embodiments, the self-made feed medium includes from about 200 mM to about 400 mM tyrosine and from about 50 mM to about 150 mM tryptophan.

In some embodiments, the self-made feed medium and the fed-batch medium are added to the cell culture at the exponential growth phase, the described fed-batch medium is selected from the following concentrated feed medium: CHO CD Efficient Feed™ A and Efficient Feed™ A+AGT Supplement, Efficient Feed™ B, Efficient Feed™ B+AGT Supplement, Efficient Feed™ C, Efficient Feed™ C+AGT Supplement, Cellvento™ Feed 200 or Acti CHO Feed A, the preferred selection is Acti CHO Feed A CD.

In some embodiments, the self-made medium and fed-batch medium are added to the culture begging at culture day 3.

In some embodiments, the self-made feed medium and fed-batch medium are added to cell culture everyday or every few days (such as every 2 to 3 days) beginning at culture day 3 for the entire culture duration time.

In some embodiments, the self-made feed medium and fed-batch medium are added to the cell culture every other day beginning at culture day 3, then days 5, 7, 9 and 11.

In some embodiments, each time the added volume of the feed medium (including the self-made feed medium and the fed-batch medium) is from about 1% to about 50% of the total volume of growth medium, the optimized percentage is from about 1% to about 20%, or from about 1% to about 10%, or from about 3% to about 6%. The growth medium volume described for cell culture is the present volume of medium in the fermentation tank or fermentation bottle prior to every addition of the feed medium.

In some embodiments, the ratio of the self-made feed medium and the fed-batch medium added to the cell culture is about 1~10:10~100, or about 1~5:10~50, or about 1~3:10~20, such as about 1:100, about 1:50, about 1:20, about 1:30, about 1:20, about 1:10, about 1.5:8.5, about 2:5, etc.

In some embodiments, each culturing is terminated when cell viability is lower than 99%, lower than 98%, lower than 97%, lower than 96%, lower than 95%, lower than 90%, lower than 85%, or lower than 80%.

The antibodies described in the present invention are all IgG1 monclonal antibody (mAb), examples of antibodies which are produced using the materials and methods of the invention include anti-tumor necrosis factor (TNF)-α antibodies and anti-vascular endothelial growth factor (VEGF) antibody.

Cysteine is a common cell culture medium component. However, there is no report in the literature describing the relationship between cysteine feed amount in cell culture and the purity of antibody. Through a creative and diligent effort, the inventors developed self-made feed media. By controlling the concentration of cysteine in self-made feed medium and the feed amount and time of addition into the cell culture, significantly improved antibody purity can be achieved, the inventor found that the application of this self-made feed medium in mammalian cell cultures expressing mAbs, more antibody molecules with correct assembly and folding are produced, and thus improving the level of purity without affecting the final antibody expression titer and glycosylation profile. These results assure the safety and efficacy of these mAb drugs. This method is simple and easy, and is suitable for large scale industrial production.

DETAILED DESCRIPTION OF THE INVENTION

The preferred embodiments of the present invention are described below, what are protected by the present invention is not limited to the following preferred embodiment. It should be pointed out when the technical personnel in the field of the invention, on the basis of conception, made a number of deformation and improvement that also belong to the scope of protection of invention.

The basal medium, feed media and reference standards used in the embodiments are available commercially. Cysteine, tyrosine and tryptophan were purchased from Sigma. CHO (Chinese hamster ovary cell) cell lines were licensed from Lonza Co., Ltd.

EXAMPLE 1

Basal Medium: commercial Medium Hycell CHO Medium (purchased from Hyclone).

Self-made feed medium: dissolving and mixing thoroughly 300 mmol tyrosine (181.2 g/mol), 280 mmol cysteine (121.15 g/mol), 100 mmol tryptophan (204.23 g/mol) in 700 ml ultrapure water without light, continue stirring for 40 min, then adding NaOH (32.1 g/L) into the solution. Stirring for another 30 min, then using 5 M NaOH to adjust pH to 10.95~11.2, continue to stir for 20 min more, then determine solution turbidity (turbidity should be less than 10 NTU), adding water to reach final volume of 1000 ml, stirring 10 more min. This solution is then filtered through a 0.22 μm membrane filter.

Fed-batch medium: commercial medium Acti CHO Feed A CD (purchased from GE).

Cell lines: A recombinant CHO cell line contains nucleic acid sequences encoding antibodies against human tumor necrosis factor (TNF) (reference to WO1997029131).

Figure 1:
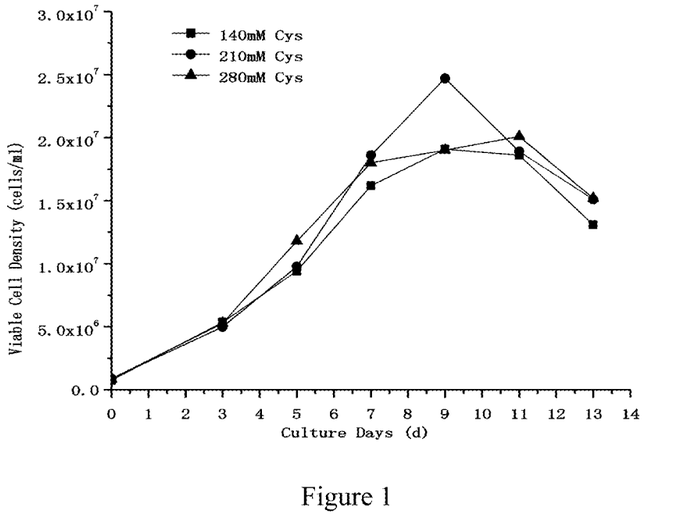
FIG. 1 depicts effect of different cysteine concentrations on viable cell density of a recombinant cell line expressing anti-TNF mAb of Examples 1-3.
Figure 2:
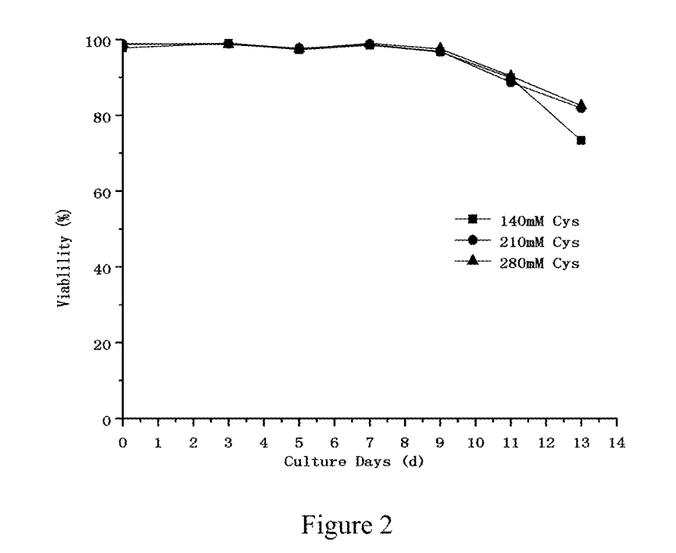
FIG. 2 depicts effect of different cysteine concentrations on cell viability of a recombinant cell line expressing anti-TNF mAb of Examples 1-3.
Figure 6:
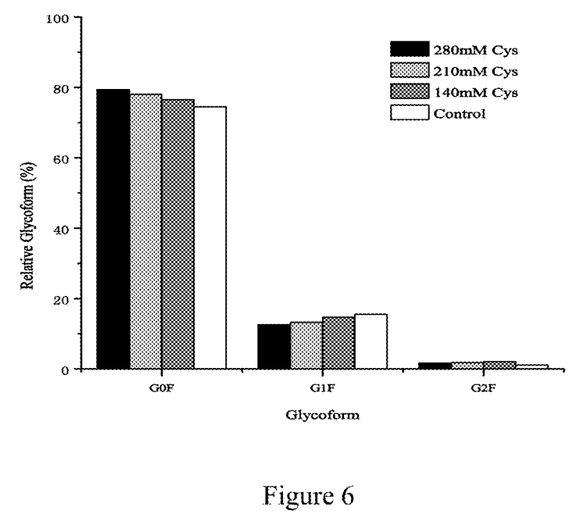
FIG. 6 depicts glycan composition of Examples 1-3 and reference standard (Adalimumab).

The cultures containing basal medium were inoculated using cells at the mid-exponential growth phase to reach an initial cell density of $0.85 \times 10^6$ cells/ml. Experiments were conducted in flasks (Corning) with a working volume of 100 ml and were shaken at 130 rpm, 37° C. with relative humidity in a 8% $CO_2$ enriched incubator. Cell density, viability, and a variety of metabolic parameters were determined daily. Based on the results of NOVA analysis of daily samples, culture glucose concentration was maintained at 6-8 g/L and L-Glutamic acid monosodium salt hydrate concentration at 4-7 mM. Fed-batch medium were added into each culture every other day at 3.5% of the present total culture volume on culture day 3 followed by 5.5% on days 5 7, 9, and 11 whereas the self-made medium were added to the culture at 0.35% on day 3 and 0.55% on days 5, 7, 9, and 11. The culture was terminated on day 13 and culture supernatants were analyzed using Protein A and high performance liquid chromatography (HPLC) to determine the antibody titer. Antibody purity was determined by capillary electrophoresis using samples from 3 steps downstream chromatographic purification, and the results are shown in table 1. Glycans were characterized using LC/MS analysis, the results are shown in FIG. 6, the standard was Adalimumab (trade name, Humira). Cell density (FIG. 1) and vitality (FIG. 2) were determined using blue trypan staining method.

EXAMPLE 2

Basal Medium: commercial Medium Hycell CHO Medium (purchased from Hyclone)

Self-made feed medium: dissolving and mixing thoroughly 300 mmol tyrosine (181.2 g/mol), 210 mmol cysteine (121.15 g/mol), 100 mmol tryptophan (204.23 g/mol) in 700 ml ultrapure water without light, continue stirring for 40 min, then adding NaOH (32.1 g/L) into the solution. Stirring for another 30 min, then using 5 M NaOH to adjust pH to 10.95~11.2, continue to stir for 20 min more, then detecting the solution turbidity (turbidity should be less than 10 NTU), adding water to reach final volume of 1000 ml, stirring 10 more min. This solution is then filtered through a 0.22 µm membrane filter.

Fed-batch medium: commercial medium Acti CHO Feed A CD (purchased from GE).

Cell lines: A recombinant CHO cell line contains nucleic acid sequences encoding antibodies against human tumor necrosis factor (TNF) (reference to WO1997029131).

The cultures containing basal medium were inoculated using cells at the mid-exponential growth phase to reach an initial cell density of 0.85×10$^6$ cells/ml. Experiments were conducted in flasks (Corning) with a working volume of 100 ml and were shaken at 130 rpm, 37° C. with relative humidity in a 8% $CO_2$ enriched incubator. Cell density, viability, and a variety of metabolic parameters were determined daily. Based on the results of NOVA analysis of daily samples, culture glucose concentration was maintained at 6-8 g/L and L-Glutamic acid monosodium salt hydrate concentration at 4-7 mM. Fed-batch medium were added into each culture every other day at 3.5% of the present total culture volume on culture day 3 followed by 5.5% on days 5 7, 9, and 11 whereas the self-made medium were added to the culture at 0.35% on day 3 and 0.55% on days 5, 7, 9, and 11. The culture was terminated on day 13 and culture supernatants were analyzed using Protein A and high performance liquid chromatography (HPLC) to determine the antibody titer. Antibody purity was determined by capillary electrophoresis using samples from 3 steps downstream chromatographic purification, and the results are shown in table 1. Glycans were characterized using LC/MS analysis, the results are shown in FIG. 6, the standard was Adalimumab (trade name, Humira). Cell density (FIG. 1) and vitality (FIG. 2) were determined using blue trypan staining method.

EXAMPLE 3

Basal Medium: commercial Medium Hycell CHO Medium (purchased from Hyclone)

Self-made feed medium: dissolving and mixing thoroughly 300 mmol tyrosine (181.2 g/mol), 140 mmol cysteine (121.15 g/mol), 100 mmol tryptophan (204.23 g/mol) in 700 ml ultrapure water without light, continue stirring for 40 min, then adding NaOH (32.1 g/L) into the solution. Stirring for another 30 min, then using 5 M NaOH to adjust pH to 10.95~11.2, continue to stir for 20 min more, then detecting the solution turbidity (turbidity should be less than 10 NTU), adding water to reach final volume of 1000 ml, stirring 10 more min. This solution is then filtered through a 0.22 µm membrane filter.

Fed-batch medium: commercial medium Acti CHO Feed A CD (purchased from GE).

Cell lines: A recombinant CHO cell line contains nucleic acid sequences encoding antibodies against human tumor necrosis factor (TNF) (reference to WO1997029131).

The cultures containing basal medium were inoculated using cells at the mid-exponential growth phase to reach an initial cell density of 0.85×10$^6$ cells/ml. Experiments were conducted in flasks (Corning) with a working volume of 100 ml and were shaken at 130 rpm, 37° C. with relative humidity in a 8% $CO_2$ enriched incubator. Cell density, viability, and a variety of metabolic parameters were determined daily. Based on the results of NOVA analysis of daily samples, culture glucose concentration was maintained at 6-8 g/L and L-Glutamic acid monosodium salt hydrate concentration at 4-7 mM. Fed-batch medium were added into each culture every other day at 3.5% of the present total culture volume on culture day 3 followed by 5.5% on days 5, 7, 9, and 11 whereas the self-made medium were added to the culture at 0.35% on day 3 and 0.55% on days 5, 7, 9, and 11. The culture was terminated on day 13 and culture supernatants were analyzed using Protein A and high performance liquid chromatography (HPLC) to determine the antibody titer. Antibody purity was determined by capillary electrophoresis using samples from 3 steps downstream chromatographic purification, and the results are shown in table 1. Glycans were characterized using LC/MS analysis, the results are shown in FIG. 6, the standard was Adalimumab (trade name, Humira). Cell density (FIG. 1) and vitality (FIG. 2) were determined using blue trypan staining method.

EXAMPLE 4

Basal Medium: commercial Medium Forti CHO AGT (purchased from Gibco)

Self-made feed medium: dissolving and mixing thoroughly 300 mmol tyrosine (181.2 g/mol), 280 mmol cysteine (121.15 g/mol), 100 mmol tryptophan (204.23 g/mol) in 700 ml ultrapure water without light, continue stirring for 40 min, then add NaOH (32.1 g/L) into the solution. Stirring for another 30 min, then using 5 M NaOH to adjust pH to 10.95~11.2, continue to stir for 20 min more, then detecting the solution turbidity (turbidity should be less than 10 NTU), add water to reach final volume of 1000 ml, stir 10 more min. This solution is then filtered through a 0.22 µm membrane filter.

Fed-batch medium: commercial medium Acti CHO Feed A CD (purchased from GE).

Cell lines: A recombinant CHO cell line contains nucleic acid sequences encoding antibodies against vascular endothelial growth factor (reference to WO1998045331).

Figure 3:
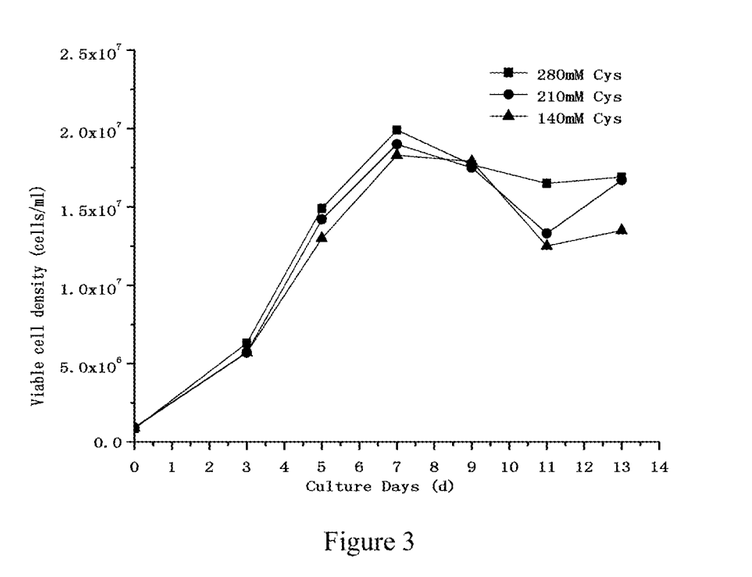
FIG. 3 depicts effect of different cysteine concentrations on viable cell density of a recombinant cell line expressing anti-VEGF mAb of Examples 4-6.
Figure 4:
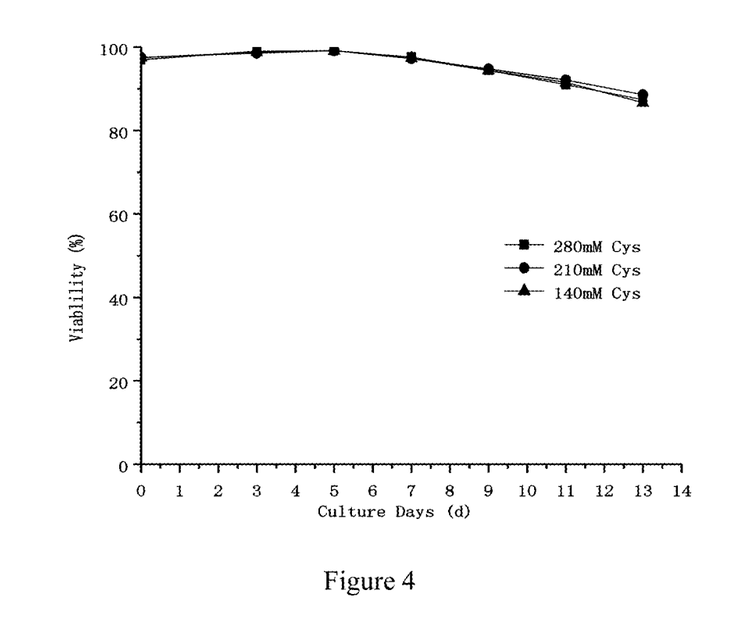
FIG. 4 depicts effect of different cysteine concentrations on cell viability of a recombinant cell line expressing anti-VEGF mAb of Examples 4-6.
Figure 5:
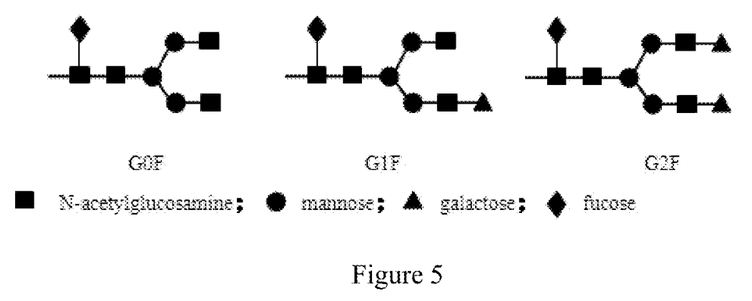
FIG. 5 depicts glycan structure diagram.
Figure 7:
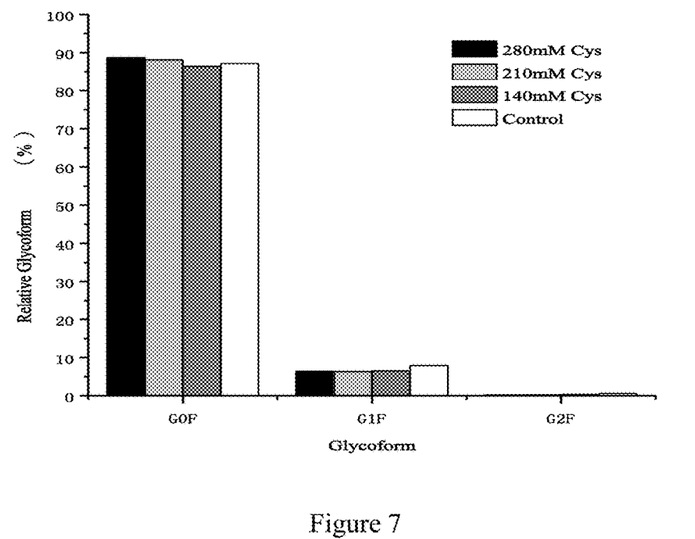
FIG. 7 depicts glycan composition of Examples 4-6 and reference standard (Bevacizumab).

The cultures containing basal medium were inoculated using cells at the mid-exponential growth phase to reach an initial cell density of 1.0×10$^6$ cells/ml. Experiments were conducted in flasks (Corning) with a working volume of 100 ml and were shaken at 130 rpm, 37° C. with relative humidity in a 8% $CO_2$ enriched incubator. Cell density, viability, and a variety of metabolic parameters were determined daily. Based on the results of NOVA analysis of daily samples, culture glucose concentration was maintained at 6-8 g/L and L-Glutamic acid monosodium salt hydrate concentration at 4-7 mM. Fed-batch medium were added into each culture every other day at 3.5% of the present total culture volume on culture day 3 followed by 5.5% on days 5 7, 9, and 11 whereas the self-made medium were added to the culture at 0.35% on day 3 and 0.55% on days 5, 7, 9, and 11. The culture was terminated on day 13 and culture supernatants were analyzed using Protein A and high performance liquid chromatography (HPLC) to determine the antibody titer. Antibody purity was determined by capillary electrophoresis using samples from 3 steps downstream chromatographic purification, and the results are shown in table 1. Glycans were characterized using LC/MS analysis, the results are shown in FIG. 7, the standard was Bevacizumab (trade name, Avastin). Cell density (FIG. 3) and vitality (FIG. 4) were determined using blue trypan staining method.

EXAMPLE 5

Basal Medium: commercial Medium Forti CHO AGT (purchased from Gibco)

Self-made feed medium: dissolving and mixing thoroughly 300 mmol tyrosine (181.2 g/mol), 210 mmol cysteine (121.15 g/mol), 100 mmol tryptophan (204.23 g/mol) in 700 ml ultrapure water without light, continue stirring for 40 min, then add NaOH (32.1 g/L) into the solution. Stirring for another 30 min, then using 5 M NaOH to adjust pH to 10.95~11.2, continue to stir for 20 min more, then detecting the solution turbidity (turbidity should be less than 10 NTU), adding water to reach final volume of 1000 ml, stirring 10 more min. This solution is then filtered through a 0.22 μm membrane filter.

Fed-batch medium: commercial medium Acti CHO Feed A CD (purchased from GE).

Cell lines: A recombinant CHO cell line contains nucleic acid sequences encoding antibodies against vascular endothelial growth factor (reference to WO1998045331).

The cultures containing basal medium were inoculated using cells at the mid-exponential growth phase to reach an initial cell density of $1.0 \times 10^6$ cells/ml. Experiments were conducted in flasks (Corning) with a working volume of 100 ml and were shaken at 130 rpm, 37° C. with relative humidity in a 8% $CO_2$ enriched incubator. Cell density, viability, and a variety of metabolic parameters were determined daily. Based on the results of NOVA analysis of daily samples, culture glucose concentration was maintained at 6-8 g/L and L-Glutamic acid monosodium salt hydrate concentration at 4-7 mM. Fed-batch medium were added into each culture every other day at 3.5% of the present total culture volume on culture day 3 followed by 5.5% on days 5, 7, 9, and 11 whereas the self-made medium were added to the culture at 0.35% on day 3 and 0.55% on days 5, 7, 9, and 11. The culture was terminated on day 13 and culture supernatants were analyzed using Protein A and high performance liquid chromatography (HPLC) to determine the antibody titer. Antibody purity was determined by capillary electrophoresis using samples from 3 steps downstream chromatographic purification, and the results are shown in table 1. Glycans were characterized using LC/MS analysis, the results are shown in FIG. 7, the standard was Bevacizumab (trade name, Avastin). Cell density (FIG. 3) and vitality (FIG. 4) were determined using blue trypan staining method.

EXAMPLE 6

Basal Medium: commercial Medium Forti CHO AGT (purchased from Gibco)

Self-made feed medium: dissolving and mixing thoroughly 300 mmol tyrosine (181.2 g/mol), 140 mmol cysteine (121.15 g/mol), 100 mmol tryptophan (204.23 g/mol) in 700 ml ultrapure water without light, continue stirring for 40 min, then add NaOH (32.1 g/L) into the solution. Stirring for another 30 min, then using 5 M NaOH to adjust pH to 10.95~11.2, continue to stir for 20 min more, then detecting the solution turbidity (turbidity should be less than 10 NTU), adding water to reach final volume of 1000 ml, stirring 10 more min. This solution is then filtered through a 0.22 μm membrane filter.

Fed-batch medium: commercial medium Acti CHO Feed A CD (purchased from GE).

Cell lines: A recombinant CHO cell line contains nucleic acid sequences encoding antibodies against vascular endothelial growth factor (reference to WO1998045331).

The cultures containing basal medium were inoculated using cells at the mid-exponential growth phase to reach an initial cell density of $1.0 \times 10^6$ cells/ml. Experiments were conducted in flasks (Corning) with a working volume of 100 ml and were shaken at 130 rpm, 37° C. with relative humidity in a 8% $CO_2$ enriched incubator. Cell density, viability, and a variety of metabolic parameters were determined daily. Based on the results of NOVA analysis of daily samples, culture glucose concentration was maintained at 6-8 g/L and L-Glutamic acid monosodium salt hydrate concentration at 4-7 mM. Fed-batch medium were added into each culture every other day at 3.5% of the present total culture volume on culture day 3 followed by 5.5% on days 5 7, 9, and 11 whereas the self-made medium were added to the culture at 0.35% on day 3 and 0.55% on days 5, 7, 9, and 11. The culture was terminated on day 13 and culture supernatants were analyzed using Protein A and high performance liquid chromatography (HPLC) to determine the antibody titer. Antibody purity was determined by capillary electrophoresis using samples from 3 steps downstream chromatographic purification, and the results are shown in table 1. Glycans were characterized using LC/MS analysis, the results are shown in FIG. 7, the standard was Bevacizumab (trade name, Avastin). Cell density (FIG. 3) and vitality (FIG. 4) were determined using blue trypan staining method.

Control 1

Basal Medium: commercial Medium Hycell CHO Medium (purchased from Hyclone)

Self-made feed medium: dissolving and mixing thoroughly 300 mmol tyrosine (181.2 g/mol) and 100 mmol tryptophan (204.23 g/mol) in 700 ml ultrapure water without light, continue stirring for 40 min, then adding NaOH (32.1 g/L) into the solution. Stirring for another 30 min, then use 5 M NaOH to adjust pH to 10.95~11.2, continue to stir for 20 min more, then detecting the solution turbidity (turbidity should be less than 10 NTU), adding water to reach final volume of 1000 ml, stirring 10 more min. This solution is then filtered through a 0.22 μm membrane filter.

Fed-batch medium: commercial medium Acti CHO Feed A CD (purchased from GE).

Cell lines: A recombinant CHO cell line contains nucleic acid sequences encoding antibodies against human tumor necrosis factor (TNF) (reference to WO1997029131).

The cultures containing basal medium were inoculated using cells at the mid-exponential growth phase to reach an initial cell density of 0.85×10⁶ cells/ml. Experiments were conducted in flasks (Corning) with a working volume of 100 ml and were shaken at 130 rpm, 37° C. with relative humidity in a 8% $CO_2$ enriched incubator. Cell density, viability, and a variety of metabolic parameters were determined daily. Based on the results of NOVA analysis of daily samples, culture glucose concentration was maintained at 6-8 g/L and L-Glutamic acid monosodium salt hydrate concentration at 4-7 mM. Fed-batch medium were added into each culture every other day at 3.5% of the present total culture volume on culture day 3 followed by 5.5% on days 5 7, 9, and 11 whereas the self-made medium were added to the culture at 0.35% on day 3 and 0.55% on days 5, 7, 9, and 11. The culture was terminated on day 13 and culture supernatants were analyzed using Protein A and high performance liquid chromatography (HPLC) to determine the antibody titer. Antibody purity was determined by capillary electrophoresis using samples from 3 steps downstream chromatographic purification, and the results are shown in table 1.

Control 2

Basal Medium: commercial Medium Forti CHO AGT (purchased from Gibco)

Self-made feed medium: dissolving and mixing thoroughly 300 mmol tyrosine (181.2 g/mol) and 100 mmol tryptophan (204.23 g/mol) in 700 ml ultrapure water without light, continue stirring for 40 min, then adding NaOH (32.1 g/L) into the solution. Stirring for another 30 min, then using 5 M NaOH to adjust pH to 10.95~11.2, continue to stir for 20 min more, then detecting the solution turbidity (turbidity should be less than 10 NTU), add water to reach final volume of 1000 ml, stir 10 more min. This solution is then filtered through a 0.22 μm membrane filter.

Fed-batch medium: commercial medium Acti CHO Feed A CD (purchased from GE).

Cell lines: A recombinant CHO cell line contains nucleic acid sequences encoding antibodies against vascular endothelial growth factor (reference to WO1998045331).

The cultures containing basal medium were inoculated using cells at the mid-exponential growth phase to reach an initial cell density of 1.0×10⁶ cells/ml. Experiments were conducted in flasks (Corning) with a working volume of 100 ml and were 385 shaken at 130 rpm, 37° C. with relative humidity in a 8% $CO_2$ enriched incubator. Cell density, viability, and a variety of metabolic parameters were determined daily. Based on the results of NOVA analysis of daily samples, culture glucose concentration was maintained at 6-8 g/L and L-Glutamic acid monosodium salt hydrate concentration at 4-7 mM. Fed-batch medium were added into each culture every other day at 3.5% of the present total culture volume on culture day 3 followed by 5.5% on days 5 7, 9, and 11 whereas the self-made medium were added to the culture at 0.35% on day 3 and 0.55% on days 5, 7, 9, and 11. The culture was terminated on day 13 and culture supernatants were analyzed using Protein A and high performance liquid chromatography (HPLC) to determine the antibody titer. Antibody purity was determined by capillary electrophoresis using samples from 3 steps downstream chromatographic purification, and the results are shown in Table 1 below.

TABLE 1

| Cell lines | Example | Cysteine concentrations of self-made feed medium | Relative titer (%) | Antibody purity (%) |
|---|---|---|---|---|
| Anti-TNFα | Example 1 | 280 mM | 100 | 94.54 |
| | Example 2 | 210 mM | 99.76 | 95.21 |
| | Example 3 | 140 mM | 93.67 | 95.8 |
| | Control 1 | 0 mM | 18.3 | 89.95 |
| Anti-VEGF | Example 4 | 280 mM | 100 | 96.91 |
| | Example 5 | 210 mM | 98.2 | 97.77 |
| | Example 6 | 140 mM | 95.8 | 98.1 |
| | Control 2 | 0 mM | 71.25 | 93.42 |

What is claimed is:

1. A self-made feed medium comprising from about 90 mM to about 500 mM of cysteine, from about 50 mM to about 500 mM of tyrosine, and from about 50 mM to about 300 mM of tryptophan, wherein the pH of the self-made feed medium is equal or greater than about 10.

2. The self-made medium according to claim 1, wherein the self-made medium comprises from about 100 mM to about 400 mM cysteine.

3. The self-made medium according to claim 1, wherein the self-made medium comprises 120 mM to 300 mM cysteine.

4. The self-made medium according to claim 1, wherein the self-made feed medium comprises from about 200 mM to about 400 mM of tyrosine, and from about 50 mM to about 150 mM of tryptophan.

5. The self-made medium according to claim 1, wherein the pH of the self-made feed medium ranges from about 10 to about 12.

6. A method for culturing mammalian cells comprising the following steps:
   1) seeding mammalian cells comprising nucleic acids encoding the antibody of interest in a basal culture medium to form a cell culture;
   2) adding the self-made feed medium of claim 1 after the cell culture entering the exponential growth phase; and
   3) monitoring cell viability and adjusting the culture duration time.

7. The method according to claim 6 characterized by further adding a fed-batch medium to the cell culture at the exponential growth phase.

8. The method according to claim 6 characterized by adding the self-made feed medium and the fed-batch medium to the cell culture every day or every 2-3 days beginning at culture day 3 for the entire culture duration time.

9. The method according to claim 8, wherein the added total volume of the self-made feed medium and the fed-batch medium is from about 1% to about 50% of the present total cell culture volume, and wherein the volume ratio of the self-made feed medium to the fed-batch medium is about 1~10:10~100.

10. The method according to claim 8, wherein the added total volume of the self-made feed medium and the fed-batch medium is from 1% to 20% of the present total cell culture volume, and wherein the volume ratio of the self-made feed medium to the fed-batch medium is about 1~3: 10~20.

11. The method according to claim 8, wherein the added total volume of the self-made feed medium and the fed-batch medium is from 1% to 10% of the present total cell culture volume, and wherein the volume ratio of the self-made feed medium to the fed-batch medium is about 1:10.

12. The method according to claim 8 characterized by adding the self-made feed medium and the fed-batch medium to the cell culture on culture day 3, 5, 7, 9 and 11.

13. The method according to claim 6, wherein when the cell viability is lower than 90%, the culturing is terminated.

* * * * *